US006796954B2

(12) United States Patent
Sawamoto et al.

(10) Patent No.: US 6,796,954 B2
(45) Date of Patent: Sep. 28, 2004

(54) METHOD FOR PREPARING LEUCOCYTE-FREE BLOOD PREPARATION AND BLOOD ADMINISTRATION SET

(75) Inventors: Jirou Sawamoto, Kanagawa (JP); Masato Kamibayashi, Kanagawa (JP); Shinji Motoyama, Kanagawa (JP)

(73) Assignee: Terumo Kabushiki Kaisha, Tokyo (JP)

(*) Notice: Subject to any disclaimer, the term of this patent is extended or adjusted under 35 U.S.C. 154(b) by 115 days.

(21) Appl. No.: 10/000,366

(22) Filed: Dec. 4, 2001

(65) Prior Publication Data

US 2002/0068893 A1 Jun. 6, 2002

(30) Foreign Application Priority Data

Dec. 4, 2000 (JP) ........................................ 2000-368095

(51) Int. Cl.[7] .......................... A61M 37/00; A61M 5/00; A61B 19/00; B01D 35/00
(52) U.S. Cl. .......................... 604/6.03; 604/6.09; 604/7; 604/6.16; 604/406; 210/348; 210/767; 435/2
(58) Field of Search .......................... 422/44; 604/4.01, 604/5.01, 6.01, 6.03, 6.05, 6.09, 6.15, 6.16, 7, 403, 406, 408, 411–13, 415; 210/645, 650–51, 767, 348, 435–37, 446, 500.1, 503; 435/2

(56) References Cited

U.S. PATENT DOCUMENTS 5,707,520 A * 1/1998 Kuroki et al. .............. 210/436

FOREIGN PATENT DOCUMENTS

| EP | 1 013 295 A1 | 6/2000 |
|---|---|---|
| WO | 98/28057 A1 | 7/1998 |
| WO | WO 98/287057 * | 7/1998 |
| WO | 99/44718 A1 | 9/1999 |
| WO | WO 99/44718 * | 9/1999 |

OTHER PUBLICATIONS

"Hypotension or Shock Developed in Blood Transfusion by Using Leukocyte Removal Filter," *Pharmaceuticals and Medical Devices Safety Information*, No. 150, Oct. 1998, Agency of Countermeasures for the Safety of Medicines, Ministry of Health and Welfare, pp. 2–5.

Ito et al., "Hypotensive Reactions Probably Attributable to Bradykinin Produced by Platelet Transfusion Through a White–Cell Reduction Filter: A Case Report," *The Journal of Japan Society for Clinical Anesthesia*, vol. 19, No. 6 (1999), pp. 414–418.

Hamaguchi "ACE Inhibitors and Negatively Charged Filters," *Biomedicine and Therapeutics*, vol. 33, No. 1 (1999), p. 74.

Noguchi et al., "Leukocyte Removal Filter–Passed Lymphocytes Produce Large Amounts of Interleukin–4 in Immunotherapy for Inflammatory Bowel Disease: Role of Bystander Suppression," *Therapeutic Apheresis*, vol. 2, No. 2 (1998), pp. 109–114.

Fried et al., "Hypotensive Reactions to White Cell–Reduced Plasma in a Patient Undergoing Angiotensin–Converting Enzyme Inhibitor Therapy," *Transfusion*, vol. 36, No. 10, Oct. 1996, pp. 900–903.

* cited by examiner

Primary Examiner—Patricia Biance
(74) Attorney, Agent, or Firm—Burns, Doane, Swecker & Mathis, L.L.P.

(57) ABSTRACT

Preparing a leucocyte-free blood by introducing a leucocyte containing liquid into a leucocyte removal filter; removing a first fraction from an effluent that is discharged from the leucocyte removal filter; obtaining an effluent portion that is discharged after the first fraction as a leucocyte-free blood preparation. A blood administration set including a leucocyte removal filter having an inlet port for introducing a leucocyte containing liquid, for separating leucocytes from the leucocyte containing liquid; and a passage for discharging a leucocyte-free blood preparation from the leucocyte removal filter. The passage has a device for removing a first fraction from an effluent discharged from the leucocyte removal filter. The method and blood administration set can avoid side effects that would otherwise occur when transfusion is performed using a leucocyte removal filter so that it is highly safe and that is simple and easy.

7 Claims, 5 Drawing Sheets

METHOD FOR PREPARING LEUCOCYTE-FREE BLOOD PREPARATION AND BLOOD ADMINISTRATION SET

BACKGROUND OF THE INVENTION

1. Field of the Invention

The present invention relates to a method for preparing leucocyte-free blood preparation and to a blood administration set.

2. Description of the Related Art

It has been known that upon transfusion of various blood preparations such as erythrocyte concentrate and platelet preparation, various side effects attributable to leucocytes mixed in the preparation occur, examples of which include fever, chill, headache, urticaria, arthralgia, blood pressure depression (hypotension), dyspnea, anaphylactic shock and so on. To prevent such defects accompanying transfusion, there has been generally used a leucocyte removal filter mainly having a porous filter membrane material such as polyester, nonwoven fabric and polyurethane.

In the leucocyte removal filter, in spite of improvements in the filter membrane material, severe cases such as abrupt hypotension and shock symptom upon use have been reported (Pharmaceuticals and Medical Devices Safety Information, No. 150 (October 1998), Agency of Countermeasures for the Safety of Medicines, Ministry of Health and Welfare, p. 2–5). Accordingly, investigation of the cause of the occurrence of such side effects and establishment of countermeasures for improvement have been important issues.

Meanwhile it has been pointed out that the occurrence of side effects when leucocyte removal filters are used is caused by the participation of bradykinin and so on (S. Ito, et al., The Journal of Japan Society for Clinical Anethesia, 19 [6] (1999) p.414–418), the induction of anaphylaxis reaction due to an increase in concentration of kinin-related substances in blood (A. Hamaguchi, Biomedicine & Therapeutics, 33[1] (1999) p.74), mass production of interleukin-4 (Noguchi, M. et al., Therapeutic Apheresis, 2[2] (1998), p.109–114) and the like.

However, when leucocyte removal filters are used, side effects such as acute hypotension and severe shock symptom may occur. Therefore, they are not fully explained by the participation of bradykinin and so on as described above or the like, and safety countermeasures for preventing side effects from occurring have not been established yet.

Therefore, there has been an increasing demand for the clarification of the causes of side effects such as hypotension and establishment of safety countermeasures for preventing the side effects from occurring.

SUMMARY OF THE INVENTION

An object of the present invention is to provide a method for preparing a leucocyte-free blood preparation that can avoid side effects that would otherwise occur when transfusion is performed using a leucocyte removal filter so that it is highly safe and that is simple and easy.

Another object of the present invention is to provide a blood administration set that can avoid side effects that would otherwise occur when transfusion is performed using a leucocyte removal filter so that it is highly safe and that can be used simply and easily.

The present inventors have made extensive study in order to achieve the above-mentioned objects. As a result, they have found out the main causative substance of side effects such as hypotension that occur when transfusion is performed using a leucocyte removal filter and further that removal of the blood component containing the causative substance to outside the system can improve the safety at the time of transfusion. The present invention has been achieved based on this discovery.

With a view to elucidate the cause of occurrence of side effects at the time of transfusion of a leucocyte-free blood preparation (hereinafter sometimes referred to simply as "blood preparation") using a leucocyte removal filter, the present inventors have made analysis of gaseous components in a blood preparation by a nitrogen oxide (hereinafter referred to also as "NO") electrode (E. Murakami, Tissue Culture Engineering, 25 (1999), p.162–163) and an oxygen electrode provided upstream and downstream of a leucocyte removal filter.

Figure 1:
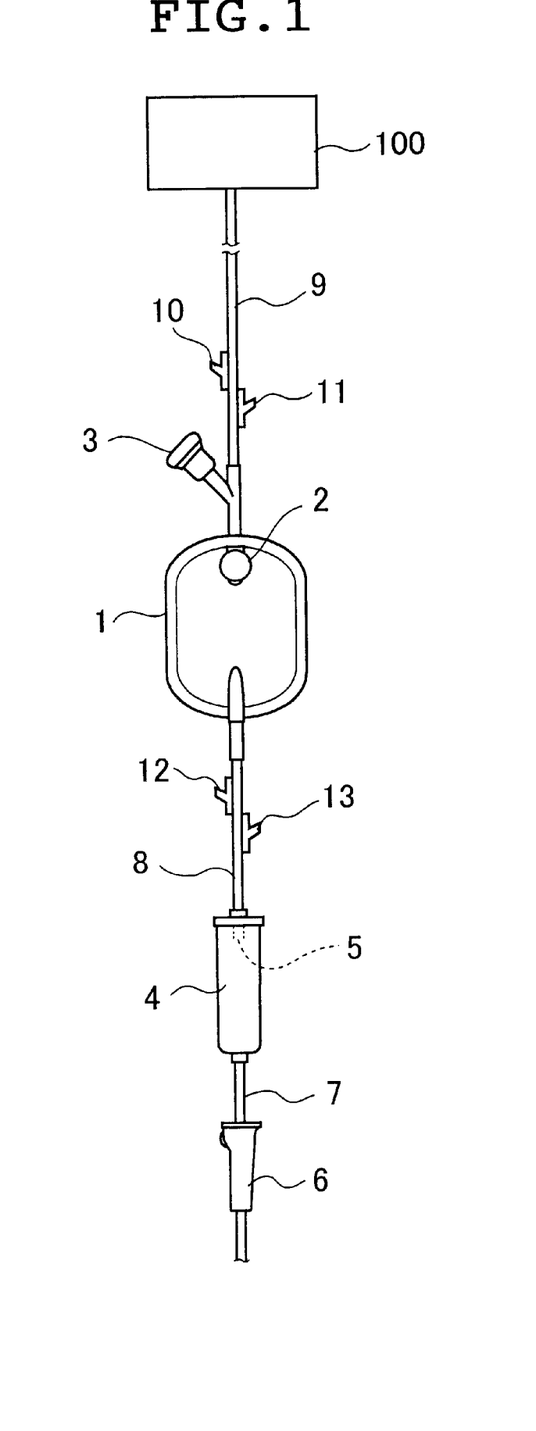
FIG. 1 is a schematic illustration of an apparatus used for the analysis of gaseous components in a blood preparation.

FIG. 1 is a schematic illustration of an apparatus used for the analysis of gaseous components in the blood preparation as described above. A leucocyte removal filter 1 is communicated with a blood bag 100 upstream thereof through a connection tube 9. The leucocyte removal filter 1 is connected with a drip chamber 4 through a connection tube 8 and a drip port 5, which is an end portion of the connection tube 8, is open inside the drip chamber 4. Downstream of the drip chamber 4 is connected a connection tube 7 provided with a clamp 6. The leucocyte removal filter 1 and the connection tube 9 upstream thereof are provided with air vents 2 and 3, respectively.

In the above apparatus, NO electrodes 10 and 12 and oxygen electrodes 11 and 13 are provided in the passages upstream and downstream of the leucocyte removal filter 1 so that the electrodes contact the liquid. The electrodes are connected to measurement apparatuses (not shown), respectively. A leucocyte containing liquid was introduced and NO concentrations and oxygen partial pressures in the liquid before and after passing the leucocyte removal filter 1 were continuously measured. Further, the blood components after passing the leucocyte removal filter 1 were administered intravenously to an animal (rabbit) and the influence thereof on blood pressure was observed.

As a result, it has been found out that among the blood components after passing the leucocyte removal filter 1, the first fraction (effluent in the first stage of filtration) tends to have considerably high NO concentration and low oxygen partial pressure, and causes hypotension.

Therefore, the present invention has been achieved based on this findings.

That is, the present invention provides a method for preparing a leucocyte-free blood preparation comprising the steps of: introducing a leucocyte containing liquid into a leucocyte removal filter; removing a first fraction from an effluent that is discharged from the leucocyte removal filter; and obtaining an effluent portion that is discharged after the first fraction as a leucocyte-free blood preparation.

Also, the present invention provides a blood administration set comprising: a leucocyte removal filter having an inlet port for introducing a leucocyte containing liquid, for separating leucocytes from the leucocyte containing liquid; and a passage for discharging a leucocyte-free blood preparation from the leucocyte removal filter; wherein the passage comprises a device for removing a first fraction from an effluent discharged from the leucocyte removal filter.

According to a preferred embodiment, the present invention provides a blood administration set as described above, wherein the device for removing the first fraction comprises:

a cylindrical casing; an inlet port provided upstream of the casing communicated with the leucocyte removal filter; an outlet port provided downstream of the casing; and a tube provided inside the casing, having one end that is liquid-tightly bonded to the casing so as to open in the outlet port of the casing and the other end that extends to a predetermined position at an interval of a first space toward the inlet port of the casing, an inner wall of the casing and an outer wall of the tube defining a second space for pooling a liquid; and preferably an absorbent provided in the second space.

According to another preferred embodiment, the present invention provides a blood administration set as described, wherein the device for removing the first fraction comprises: a cylindrical casing; an inlet port provided upstream of the casing communicated with the leucocyte removal filter; an outlet port provided downstream of the casing; a tube provided inside the casing, having one end that is liquid-tightly bonded to the casing so as to open in the inlet port of the casing and the other end that extends to a predetermined position at an interval of a first space toward the outlet port of the casing, an inner wall of the casing and an outer wall of the tube defining a second space for pooling a liquid; and an absorbent provided in the second space.

According to a still another preferred embodiment, the present invention provides a blood administration set as described above, wherein the device for removing the first fraction comprises: a branched tube having an inlet tube communicated with the leucocyte removal filter, a first branch and a second branch communicated with the inlet tube; and a clamp provided downstream of the first branch; and preferably a connection tube communicated with the second branch; a bag communicated with the connection tube; and a clamp provided with the connection tube.

According to a yet another preferred embodiment, the present invention provides a blood administration set as described above, wherein the device for removing the first fraction comprises: a two-way cock having an inlet port communicated with the leucocyte removal filter, a first outlet port, and a second outlet port; and preferably a connection tube communicated with the second outlet port; and a bag communicated with the connection tube.

According to the method of preparing a leucocyte-free blood preparation according to the present invention, side effects that would otherwise occur when transfusion is performed using a leucocyte removal filter can be avoided so that it is very highly safe. Furthermore, the method for preparing a leucocyte-free blood preparation according to the present invention is simple and easy. For these reasons, the method for preparing a leucocyte-free blood preparation according to the present invention is very useful.

The blood administration set of the present invention can be preferably used in the method for preparing a leucocyte-free blood preparation according to the present invention. Furthermore, the blood administration set of the present invention can be used simply and easily. For these reasons, the blood administration set of the present invention is very useful.

DETAILED DESCRIPTION OF THE INVENTION

Hereinafter, the present invention will be illustrated in detail with reference to the attached drawings.

A first embodiment of the present invention relates to a method for preparing a leucocyte-free blood preparation comprising the steps of: introducing a leucocyte containing liquid into a leucocyte removal filter; removing a first fraction from an effluent that is discharged from the leucocyte removal filter; and obtaining an effluent portion that is discharged after the first fraction as a leucocyte-free blood preparation.

The leucocyte removal filter used in the first embodiment is not particularly limited and any known filter may be used.

The shape of the leucocyte removal filter is not particularly limited. For example, porous body, filament, nonwoven fabric, particle, film, sheet, tube, hollow fiber, and powder may be adopted. Among these, porous body and nonwoven fabric are preferred.

The porous body preferably has a mean pore diameter of 1 $\mu$m to 20 $\mu$m as measured by use of a palm porosimeter. If the mean pore diameter is less than 1 $\mu$m, the filter tends to be clogged. On the other hand, if it is beyond 20 $\mu$m, the leucocyte removal rate explained hereinbelow might be decreased to 50% or less.

The material of the leucocyte removal filter includes, for example, natural polymers such as cotton and hemp; synthetic polymers such as nylon, polyester, polyacrylonitrile, polyolefin, halogenated polyolefin, polyethylene terephthalate, polyurethane, polyamide, polysulfone, polyethersulfone, poly(meth)acrylate, ethylene/polyvinyl alcohol copolymer, and butadiene/acrylonitrile copolymer; and mixtures thereof.

Among these, polyurethane is preferred in the case where the leucocyte removal filter is shaped into a porous body. In the case where it is shaped into a nonwoven fabric, polyethylene phthalate is preferred.

The leucocyte containing liquid is not particularly limited and includes blood preparations such as, for example, whole blood, platelet concentrate (PC), platelet rich plasma (PRP), erythrocyte concentrate, platelet component solution. The blood preparations may contain chemicals such as anticoagulant and preservative.

In the first embodiment of the present invention, the above-mentioned leucocyte containing liquid is introduced into the leucocyte removal filter and the first fraction from the effluent that is discharged from the leucocyte removal filter is removed.

As described above, the present inventors have found out that the first fraction from the effluent that is discharged from the leucocyte removal filter has high NO concentration than the effluent portion that is discharged after the first fraction, and it would be highly possible that administration of the initial effluent into the body could cause side effects such as hypotension. Thus, they have achieved the present invention based on this discovery. In the method for preparing a leucocyte-free blood preparation according to the present invention, the first fraction that could have high NO concentration is removed, and the effluent portion that is discharged after the first fraction is obtained as a leucocyte-free blood preparation, so that the danger that side effects such as hypotension could be caused upon transfusion can be prevented.

The term "first fraction" as used herein refers to all or part of components of an effluent in the first stage of filtration that turn in color from colorless transparent to dark red. In the first embodiment of the present invention, the amount of the first fraction to be removed may be determined optionally depending on a patient who receives transfusion and pathologic status thereof. Also, in the first embodiment of the present invention, the amount of the first fraction to be removed may be determined based on experiments by use of mammalians such as rabbit, rat, dog, cat, pig, goat, sheep, monkey, and ferret.

In the first embodiment of the present invention, it is preferred to remove the effluent portion that is discharged from the leucocyte removal filter during the period from the initiation of filtration to the stage where the NO concentration is decreased to at least 6 $\mu$mol/L, more preferably to the NO concentration of the leucocyte containing liquid prior to the filtration, as the first fraction.

By removing the effluent portion discharged until at least the NO concentration is decreased to 6 $\mu$mol/L as the first fraction and obtaining the effluent portion that is discharged after the first fraction as a leucocyte-free blood preparation, side effects such as hypotension due to the effluent having high NO concentration can be avoided.

Also, in the first embodiment of the present invention, it is preferred to remove the effluent portion that is discharged from the leucocyte removal filter during the period from the initiation of filtration to at least the stage where the oxygen partial pressure increases to 75% of that of the leucocyte containing liquid prior to the filtration, as the first fraction.

According to one preferred mode in the first embodiment of the present invention, the amount of the first fraction to be removed is determined by measuring NO concentration and/or oxygen partial pressure. By measuring the NO concentration and/or the oxygen partial pressure to determine the amount of the first fraction to be removed, the loss of the leucocyte containing liquid used for preparing a leucocyte-free blood preparation can be maintained at low levels.

For the measurement of NO concentration and/or oxygen partial pressure, conventional sensors may be used respectively. The type, number and measurement site of sensors can be determined appropriately depending on the purpose.

The sensor used for the measurement of NO concentration is preferably one that can measure the NO concentration in liquid immediately and continuously. For example, the sensor having detection mechanism/determination mechanism based on the chemiluminescence method or the electrode method may be used.

The sensor used for the measurement of oxygen partial pressure is preferably one that can measure the oxygen partial pressure in a liquid immediately and continuously. For example, $PO_2$-100DW manufactured by Intermedical Co. may be used.

In the first embodiment of the present invention, in addition to the above-mentioned ones, various sensors such as pH sensor may also be used. Also, these sensors may be conventional sensors, preferably those that can measure immediately and continuously.

Also, in the first embodiment of the present invention, the amount of the first fraction to be removed may vary depending on the type of the material of the leucocyte removal filter, but may be determined to be 1/50 to 1/10 time the volume of the leucocyte removal filter used.

The method of removing the first fraction is not particularly limited.

For example, a method of absorbing the first fraction by an absorbent and a method of fractionating the first fraction from subsequent effluent may be used. More specifically, there may be used the device 210 in FIG. 2, 310 in FIG. 3, 410 in FIG. 4 and 510 in FIG. 5 for removing the first fraction in the specific example of the blood administration set according to a second embodiment of the present invention explained hereinbelow.

The leucocyte-free blood preparation obtained in accordance with the first embodiment of the present invention preferably has the NO concentration of 6 $\mu$mol/L or less and more preferably has the NO concentration that is the NO concentration prior to the filtration or less. If the NO concentration of the leucocyte-free blood preparation is 6 $\mu$mol/L or less, side effects hardly occur. That is, leucocyte-free blood preparation having the NO concentration of 6 $\mu$mol/L or less is one mode of the present invention.

The apparatus used in the method for preparing the leucocyte-free blood preparation according to the first embodiment of the present invention is not particularly limited but it is preferable that the blood administration set according to the second embodiment of the present invention be used.

The second embodiment of the present invention relates to a blood administration set that comprises: a leucocyte removal filter having an inlet port for introducing a leucocyte containing liquid, for separating leucocytes from the leucocyte containing liquid; and a passage for discharging a leucocyte-free blood preparation from the leucocyte removal filter; wherein the passage comprises a device for removing a first fraction from an effluent that is discharged from the leucocyte removal filter. By use of the blood administration set according to the second embodiment of the present invention, removal of the first fraction can be performed readily and safely, so that the blood administration set according to the second embodiment of the present invention is very useful.

Hereinafter, the second embodiment of the present invention will be illustrated in detail with reference to the accompanying drawings. However, it should be noted that the present invention is not limited thereto.

Figure 2A:
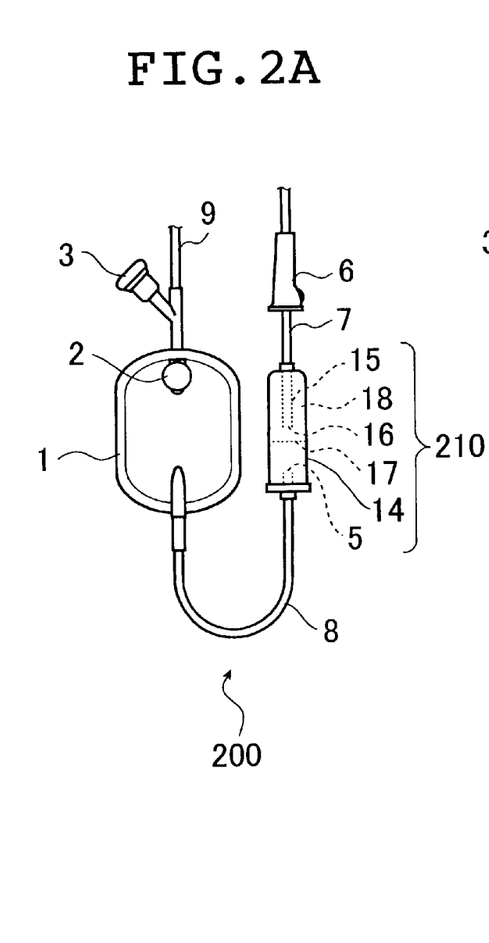
FIG. 2A is a schematic illustration of a blood administration set according to a preferred embodiment of the present invention, illustrating how to use it, illustrating the blood administration set in the state prior to introduction of a leucocyte containing liquid into a leucocyte removal filter.
Figure 2B:
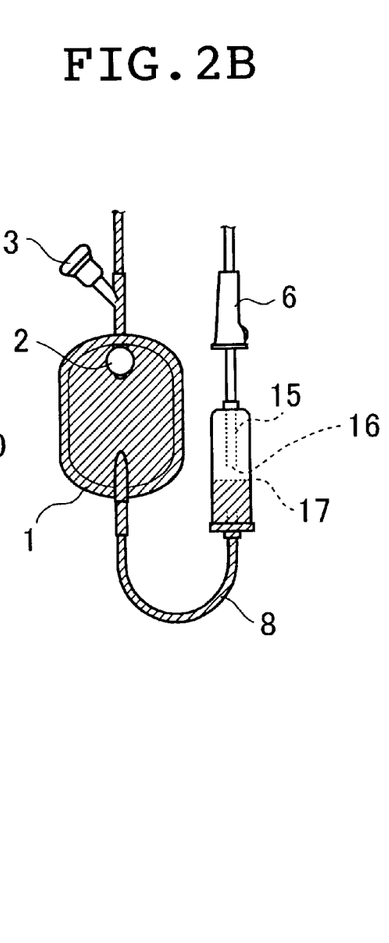
FIG. 2B is a schematic illustration of a blood administration set according to a preferred embodiment of the present invention, illustrating how to use it, illustrating the blood administration set after initiating the introduction of a leucocyte containing liquid into a leucocyte removal filter.
Figure 2C:
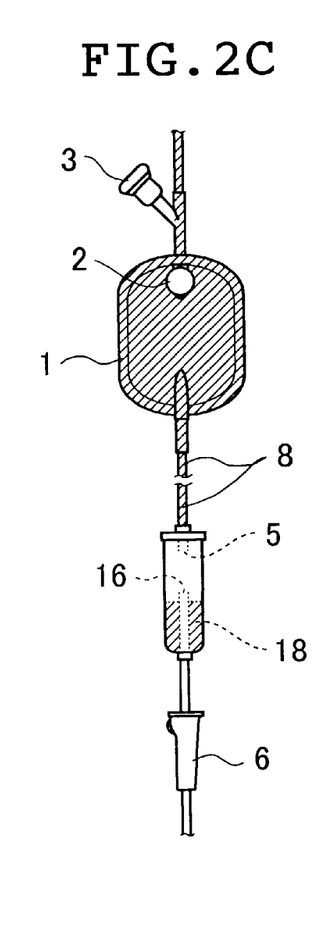
FIG. 2C is a schematic illustration of a blood administration set according to a preferred embodiment of the present invention, illustrating how to use it, illustrating the blood administration set immediately before initiating transfusion.

The blood administration set illustrated in the schematic diagram shown in FIGS. 2A, 2B and 2C is a blood administration set 200 that comprises a leucocyte removal filter 1 having an inlet port for introducing a leucocyte containing liquid, for separating leucocytes from the leucocyte containing liquid, and a passage for discharging a leucocyte-free blood preparation from the leucocyte removal filter 1; wherein the passage comprises a device 210 for removing the first fraction from the effluent that is discharged from the leucocyte removal filter 1.

The leucocyte removal filter 1 is communicated with a blood bag (not shown) located upstream thereof through a connection tube 9. The leucocyte removal filter 1 is communicated with the device 210 for removing the first fraction located downstream thereof through a connection tube 8. Downstream of the device 210 for removing the first fraction is connected a connection tube 7 provided with a clamp 6. The leucocyte removal filter 1 and the connection tube 9 upstream thereof are provided with air vents 2 and 3, respectively.

As one preferred mode of the blood administration set according to the present invention, there is provided a blood administration set 200 having a device 210 for removing the first fraction as shown in FIGS. 2A, 2B and 2C. That is, in this mode, the device 210 comprises: a cylindrical casing 14; an inlet port provided upstream of the casing 14 communicated with the leucocyte removal filter 1; an outlet port provided downstream of the casing 14; and a tube 15 provided inside the casing 14. One end of the tube 15 is liquid-tightly bonded to the casing 14 so as to open in the outlet port of the casing 14. The other end of the tube 15 extends to a predetermined position at an interval of a first space toward the inlet port of the casing 14. The inner wall of the casing 14 and the outer wall of the tube 15 define a second space or liquid pool space 18, for pooling a liquid. Preferably, an absorbent is provided in the second space 18.

As shown in FIG. 2A, the device 210 for removing the first fraction includes: a drip chamber 14 having a scale 17 thereon; a drip port 5, which is an end portion of the connection tube 8 that is open inside the drip chamber 14; and a tube 15 provided inside the drip chamber 14 along the longitudinal axis thereof. The term "drip chamber" as used herein refers to a cylindrical casing which has a structure wherein blood preparation can drop down inside thereof. The scale 17 indicates a limit for liquid pool when the drip chamber 14 is in an inverted state upside down (the state in which the connection tube 7 is upside and the connection tube 8 is downside as shown in FIG. 2B). It determines a maximum pool amount of liquid. The length of the tube 15 is set as follows. After pooling the maximum pool amount of liquid, the drip chamber 14 is returned to a normal state with respect to the upside and downside relationship (where the connection tube 7 is downside and the connection tube 8 is upside as shown in FIG. 2C). In this instance the liquid is pooled in the liquid pool space 18 defined by the inner wall of the drip chamber 14 and the outer wall of the tube 15. The length of the tube 15 is set such that a distal end 16 of the tube 15 is projected above the level of the liquid pooled in liquid pool space 18.

The liquid pool space 18 may optionally be provided with an absorbent as desired. This enables the first fraction to be absorbed and kept therein, so that removal of the first fraction from the leucocyte-free blood preparation can be facilitated.

The absorbent used in the first embodiment of the present invention is not particularly limited as far as it can absorb blood preparations. Examples of the absorbent include cellulose (for example, pulp or absorbent paper), gelatin, thrombin, oxidized cellulose, sodium alginate, tranexamic acid, ε-aminocaproic acid, adrenochrome monoaminoguanidine mesilate, sodium carbazochromium sulfonate, monoethanolamine oleate, polyvinyl alcohol/polyacrylic acid-based polymer (for example, crosslinked polyacrylic acid polymer), polyethylene oxide-based polymer, polyacrylamide-based polymer, poval-based polymer, starch-based polymer (for example, starch/polyacrylic acid graft polymer or carboxymethylated starch-based polymer), cellulose-based polymer (for example, hydroxypropylcellulose (HPC) or carboxymethylated cellulose (CMC-Na)), amino acid-based water absorbing polymer (for example, crosslinked aspartic acid-based polymer such as crosslinked polyaspartic acid; Natto resin) and so forth.

These may be used singly or two or more of them may be used in combination.

The absorbent preferably is one that absorbs water in 2 to 1000 times the weight of the absorbent itself at temperatures from ambient temperature to a temperature in the vicinity of the body temperature.

The use amount of the absorbent may vary depending on the type of the absorbent but generally it is preferably 0.01 to 2 g per 5 mL of the first fraction.

These absorbents may be employed by use of a suitable means selected from mixing, kneading, impregnation, bonding, vapor deposition, sintering, coating, distillation and the like.

More specifically, the absorbent loaded on a carrier (for example, a porous body or a sintered porous body) in the form of, for example, powder, particle, crystal, filament, film, nonwoven fabric, sponge, cotton, cylinder, filter paper or the like may be provided in the liquid pool space 18. In the case where a sintered porous body is used as the carrier, the absorbent may be loaded on the sintered porous body by mixing the absorbent with the components that constitute the sintered porous body and forming porous body for absorption and/or filter. Specifically, an absorbent such as water swelling polymer material may be molded into a desired shape by: uniformly dispersing an absorbent in a thermoplastic resin or the like before molding and mixing therewith, charging the resulting mixture in a mold; and heating and processing it or the like. A preferred example of the absorbent thus obtained includes a cylindrical porous sintered body of polyethylene containing crosslinked polyacrylic polymer.

Furthermore, those absorbents made of water-absorbing polymers, porous absorbents and so forth that can form a three-dimensional structure by itself, they may be provided in the liquid pool space 18 directly.

The absorbent may be provided by: a method in which it is inserted in the liquid pool space 18 alone or in a state where it is loaded by a carrier; a method in which it is coated on the inner wall of the liquid pool space 18, or the like. It may be provided not only in the liquid pool space 18, but also coated on the connection tube 8 that the effluent discharged from the leucocyte removal filter 1 contacts.

In the case where the absorbent is provided in the liquid pool space 18, a stopper (not shown) having a continuous or non-continuous projected structure or a stopper that a liquid permeates through readily may be provided at the position of the scale 17 of the drip chamber 14 or in the vicinity thereof in order to prevent the fall or movement of the absorbent.

Hereinafter, how to use the blood administration set 200 shown in FIGS. 2A, 2B and 2C is illustrated.

First, as shown in FIG. 2A, the clamp 6 is opened according to the conventional method in a state where the drip chamber 14 is inverted upside down so that a leucocyte containing liquid can be introduced into the leucocyte removal filter 1. As shown in FIG. 2B, the effluent from the leucocyte removal filter 1 is pooled such that it does not go beyond the position of the scale 17, and the clamp 6 is closed. Subsequently, as shown in FIG. 2C, the drip chamber 14 is returned to a normal position with respect to the upside and downside relationship and the effluent is pooled in the liquid pool space 18. In this manner, the first fraction is removed at the time of priming operation. Thereafter, the clamp 6 is opened and transfusion is initiated. Besides, in the present invention, there's no need to use priming solution for priming operation.

This method may involve the possibility of contamination of some amount of the first fraction that has been pooled and removed upon transfusion. However, it can prevent the occurrence of side effects due to transfusion so that it is useful.

In the case where an absorbent is provided in the liquid pool space 18, the drip chamber 14 is returned to a normal state with respect to upside and downside relationship and the effluent is pooled in the liquid pool space 18 in the above operation. As a result the absorbent absorbs the effluent therein.

This method enables one to catch and remove the first fraction substantially completely and suppress the side effects due to transfusion from the occurrence so that it is useful.

Figure 3A:
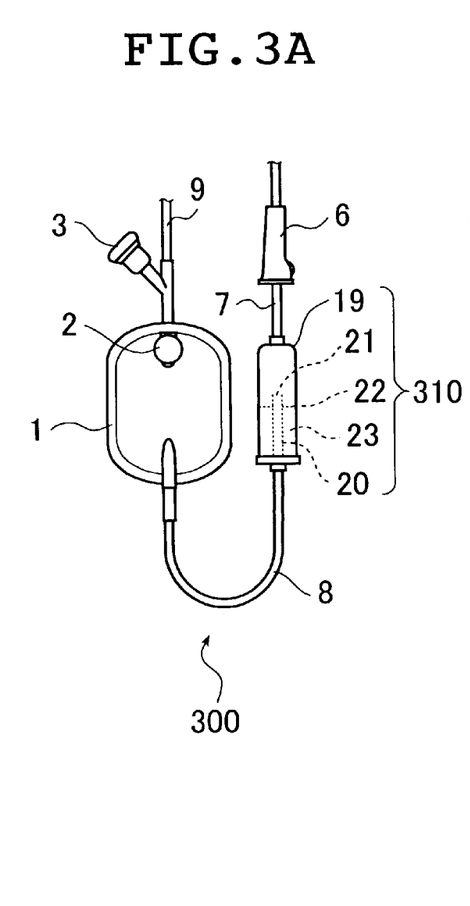
FIG. 3A is a schematic illustration of a blood administration set according to another preferred embodiment of the present invention, illustrating how to use it, illustrating the blood administration set in the state prior to introduction of a leucocyte containing liquid into a leucocyte removal filter.
Figure 3B:
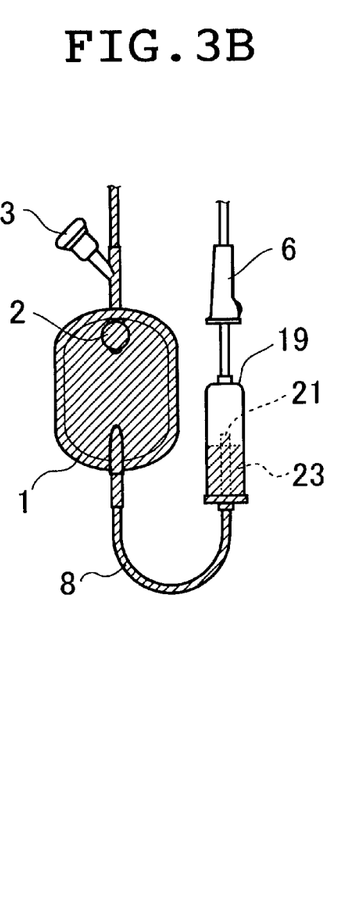
FIG. 3B is a schematic illustration of a blood administration set according to another preferred embodiment of the present invention, illustrating how to use it, illustrating the blood administration set after initiating the introduction of a leucocyte containing liquid into a leucocyte removal filter.
Figure 3C:
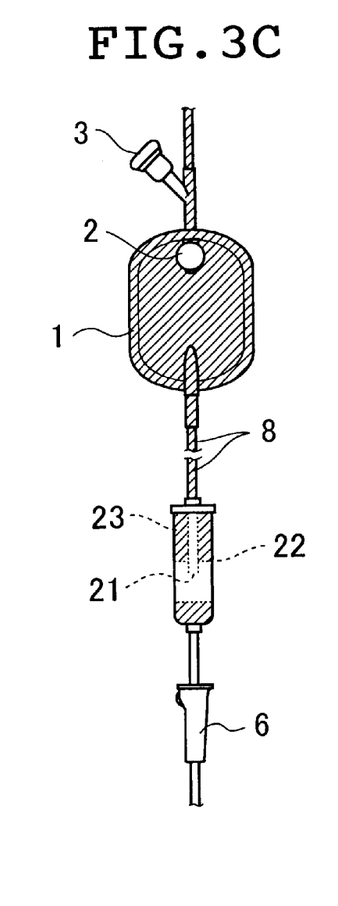
FIG. 3C is a schematic illustration of a blood administration set according to another preferred embodiment of the present invention, illustrating how to use it, illustrating the blood administration set immediately before initiating transfusion.

The blood administration set illustrated in the schematic diagram shown in FIGS. 3A, 3B and 3C is a blood administration set 300 that comprises a leucocyte removal filter 1 having an inlet port for introducing a leucocyte containing liquid, for separating leucocytes from the leucocyte containing liquid, and a passage for discharging a leucocyte-free blood preparation from the leucocyte removal filter 1; wherein the passage comprises a device 310 for removing the first fraction from the effluent that is discharged from the leucocyte removal filter 1.

The leucocyte removal filter 1 is communicated with a blood bag (not shown) located upstream thereof through a connection tube 9. The leucocyte removal filter 1 is communicated with the device 310 for removing the first fraction located downstream thereof through a connection tube 8. Downstream of the device 310 for removing the first fraction is connected a connection tube 7 provided with a clamp 6. The leucocyte removal filter 1 and the connection tube 9 upstream thereof are provided with air vents 2 and 3, respectively.

As one preferred mode of the blood administration set according to the present invention, there is provided a blood administration set 300 having a device 310 for removing the first fraction as shown in FIGS. 3A, 3B and 3C. That is, in this mode, the device 310 comprises: a cylindrical casing 19; an inlet port provided upstream of the casing 19 communicated with the leucocyte removal filter 1; an outlet port provided downstream of the casing 19; and a tube 20 provided inside the casing 19. One end of the tube 20 is liquid-tightly bonded to the casing 19 so as to open in the inlet port of the casing 19. The other end of the tube 20 extends to a predetermined position at an interval of a first space toward the outlet port of the casing 19. The inner wall of the casing 19 and the outer wall of the tube 20 define a second space or liquid pool space 23, for pooling a liquid.

As shown in FIG. 3A, the device 310 for removing the first fraction includes: a drip chamber 19 having a scale 22 thereon; and a tube 20. The tube 20 is communicated with the connection tube 8, provided inside the drip chamber 19 along the longitudinal axis thereof and provided with a drip port 21. The drip port is a distal end that is open inside the drip chamber 19. The scale 22 indicates a limit for liquid pool when the drip chamber 19 is in an inverted state upside down (the state in which the connection tube 7 is upside and the connection tube 8 is downside as shown in FIG. 3B). It determines a maximum pool amount of liquid. The length of the tube 20 is set as follows. When pooling the maximum pool amount of liquid, the liquid is pooled in the liquid pool space 23 defined by the inner wall of the drip chamber 19 and the outer wall of the tube 20. The length of the tube 20 is set such that a distal end 21 of the tube 20 is projected above the level of the liquid pooled in liquid pool space 23.

The liquid pool space 23 is provided with an absorbent. The type of the absorbent and use thereof or the like are the same as those used in case of the blood administration set 200 in the FIGS. 2A, 2B and 2C.

Hereinafter, how to use the blood administration set 300 shown in FIGS. 3A, 3B and 3C is illustrated.

First, as shown in FIG. 3A, the clamp 6 is opened according to the conventional method in a state where the drip chamber 19 is inverted upside down so that a leucocyte containing liquid can be introduced into the leucocyte removal filter 1. As shown in FIG. 3B, the effluent from the leucocyte removal filter 1 is pooled in the liquid pool space 23 and the liquid pooled is absorbed by the absorbent provided in the liquid pool space 23. The effluent from the leucocyte removal filter 1 is pooled such that it does not go beyond the position of the scale 22. After completion of the absorption by the absorbent, the clamp 6 is closed. Subsequently, as shown in FIG. 3C, the drip chamber 19 is returned to a normal position with respect to the upside and downside relationship. In this manner, a first fraction is removed at the time of priming operation. Thereafter, the clamp 6 is opened and transfusion is initiated.

This method is useful since it can considerably suppress abrupt occurrence of side effects due to transfusion by catching and removing most part of the first fraction.

Figure 4:
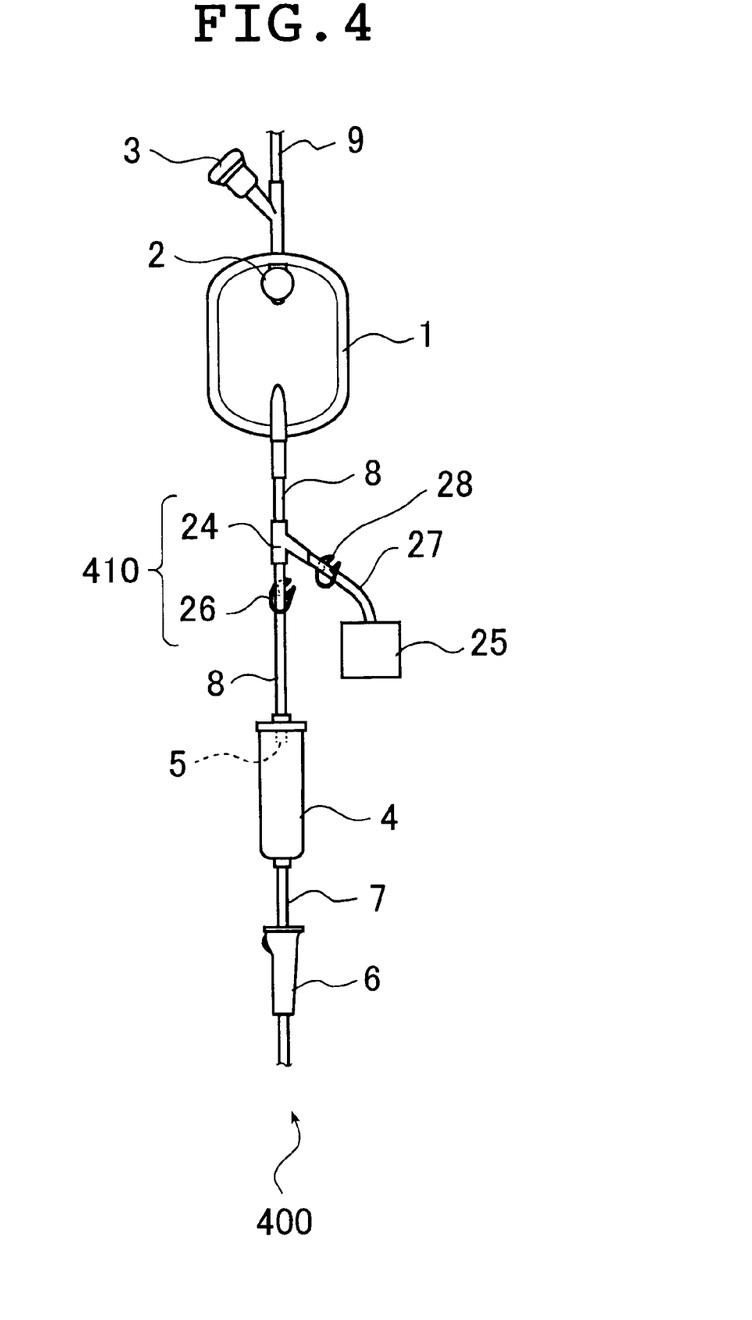
FIG. 4 is a schematic illustration of a blood administration set according to another preferred embodiment of the present invention.

The blood administration set illustrated in the schematic diagram shown in FIG. 4 is a blood administration set 400 that comprises a leucocyte removal filter 1 having an inlet port for introducing a leucocyte containing liquid, for separating leucocytes from the leucocyte containing liquid, and a passage for discharging a leucocyte-free blood preparation from the leucocyte removal filter 1; wherein the passage comprises a device 410 for removing the first fraction from the effluent discharged from the leucocyte removal filter 1.

The leucocyte removal filter 1 is communicated with a blood bag (not shown) located upstream thereof through a connection tube 9. The leucocyte removal filter 1 is communicated with the drip chamber 4 located downstream thereof through a connection tube 8. Downstream of the drip chamber 4 is connected a connection tube 7 provided with a clamp 6. The leucocyte removal filter 1 and the connection tube 9 upstream thereof are provided with air vents 2 and 3, respectively.

As one preferred mode of the blood administration set according to the present invention, there is provided a blood administration set 400 having a device 410 for the removing the first fraction as shown in FIG. 4. That is, in this mode, the device 410 comprises a branched tube 24 having first and second branches, and a clamp 26 provided downstream of the first branch. Preferably, the device 410 further includes a connection tube 27 communicated with the second branch, a bag 25 communicated with the connection tube 27, and a clamp 28 provided with the connection tube 27.

The connection tube 8 has two parts, i.e., an upstream part and a downstream part, between which the branched tube 24 is inserted. One branch of the branched tube 24 that is not communicated with the downstream part of the connection tube 8 is communicated with the connection tube 27 and is connected to the bag 25. The connection tube 27 is provided with one-touch (single action) clamp 28 immediately after the connection part with the branched tube 24. At the downstream part of the connection tube 8 is provided the single action clamp 26. The branched tube 24 and the single action clamp 26 constitute the device 410 for removing the first fraction. The device 410 optionally includes the connection tube 27, single action clamp 28 and the bag 25.

Absorbents, blood coagulant or the like may be provided inside the bag 25. The same absorbents as those used in the case of the blood administration set 200 shown in FIG. 2A, 2B and 2C may be used. The material that constitutes the bag 25 is not particularly limited in the composition, properties and so forth.

Hereinafter, how to use the blood administration set 400 shown in FIG. 4 is illustrated.

First, a leucocyte containing liquid is introduced into the leucocyte removal filter 1 in the state where the single action clamp 26 is closed and the single action clamp 28 is open. The effluent from the leucocyte removal filter 1 is pooled in the bag 25. In the case where an absorbent is placed in the bag 25, the effluent is absorbed by the absorbent. After completion of the discharge of the first fraction, the single action clamp 28 is closed and the single action clamp 26 is opened and further the clamp 6 is opened. Then, transfusion is initiated.

This method is useful since it can considerably suppress abrupt occurrence of side effects due to transfusion by catching and removing most part of the first fraction.

Furthermore, the air together with the first fraction is removed into the bag 25 so that the priming operation can be eliminated.

In the blood administration set 400 as shown in FIG. 4, the branched tube 24, the connection tube 27 and the bag 25 are provided at the connection tube 8 upstream of the drip chamber 4. Alternatively, they may be provided at the connection tube 7 downstream of the drip chamber 4. In the latter case, after performing the priming operation by inverting the drip chamber 4, the first fraction is flown into the bag 25. In the case where the drip chamber 4 is a drip chamber provided with an air removal needle, the priming operation can be achieved by flowing blood into the drip chamber 4 as it is without inverting the drip chamber 4.

Figure 5:
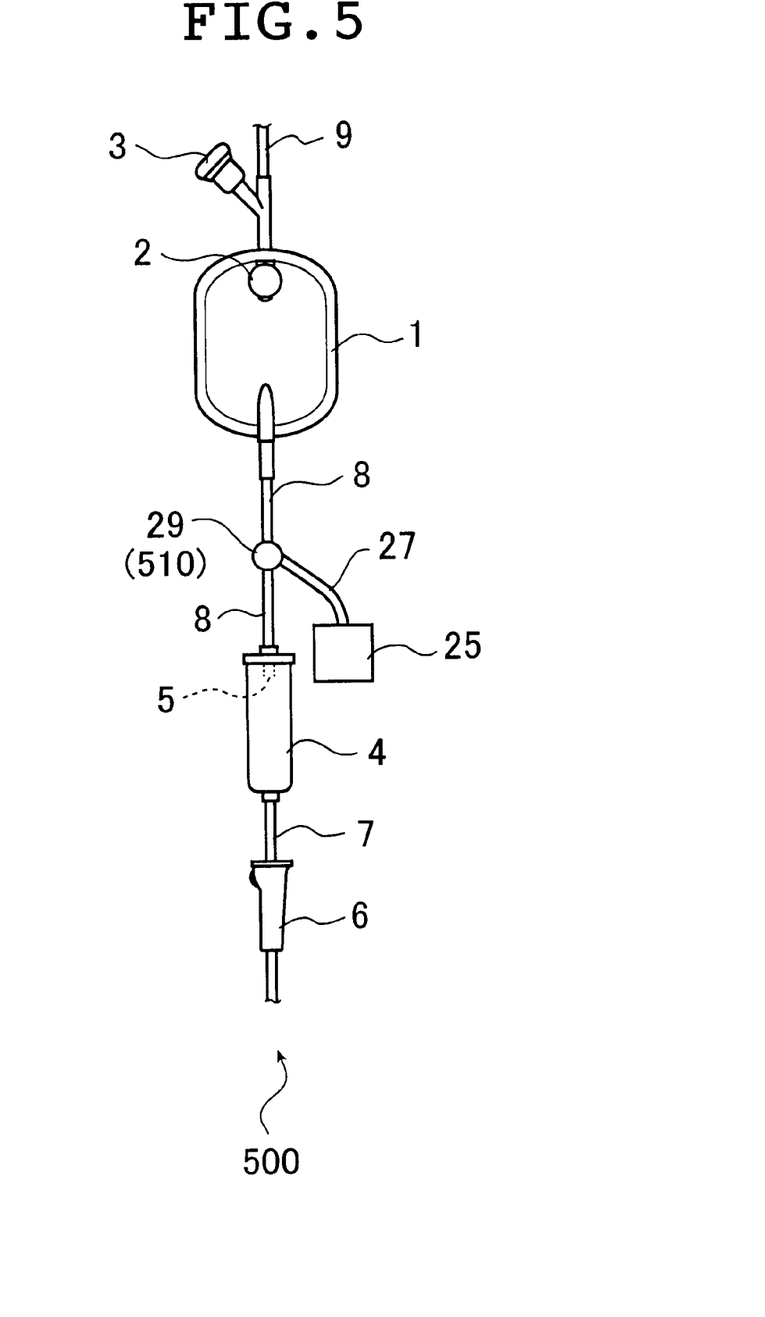
FIG. 5 is a schematic illustration of a blood administration set according to still another preferred embodiment of the present invention.

The blood administration set illustrated in the schematic diagram shown in FIG. 5 is a blood administration set that includes a two-way cock 29 for switching passages in place of the branched tube 24 and the single action clamp 26 in the blood administration set 400 as sown in FIG. 4. The two-way cock 29 constitutes a device 510 for removing the first fraction. The blood administration set 500 as shown in FIG. 5 has the same structure as the blood administration set 400 as shown in FIG. 4 except for the above-described features.

As one preferred mode of the blood administration set according to the present invention, there is provided a blood administration set 500 having a device 510 for removing the first fraction as shown in FIG. 5. That is, in this mode, the device 510 comprises a two-way cock 29 having an inlet port communicated with the leucocyte removal filter 1, a first outlet port and a second outlet port. Preferably, it further includes a connection tube 27 that is communicated with the second outlet port and a bag 25 that is communicated with the connection tube 27.

As the device for removing the first fraction, the branched tube and single action clamp as shown in FIG. 4 or the two-way cock as shown in FIG. 5 may be selected depending on the purpose.

Hereinafter, how to use the blood administration set 500 shown in FIG. 5 is illustrated.

First, a leucocyte containing liquid is introduced into the leucocyte removal filter 1 in the state where the two-way cock 29 is communicated with the connection tube 27. The effluent from the leucocyte removal filter 1 is pooled in the bag 25. In the case where an absorbent is placed in the bag 25, the effluent is absorbed by the absorbent. After completion of the discharge of the first fraction, the two-way cock 29 is set in the state where it is communicated with the connection tube 8 and further the clamp 6 is opened. Then, transfusion is initiated.

This method is useful since it can considerably suppress abrupt occurrence of side effects due to transfusion by catching and removing most part of the first fraction.

Furthermore, the air together with the first fraction is removed into the bag 25 so that the priming operation can be eliminated.

In the blood administration set 500 as shown in FIG. 5, the two-way cock 29, connection tube 27 and the bag 25 are provided at the connection tube 8 upstream of the drip chamber 4. Alternatively, they may be provided at the connection tube 7 downstream of the drip chamber 4. In the latter case, after performing the priming operation by inverting the drip chamber 4, the first fraction is flown into the bag 25. In the case where the drip chamber 4 is a drip chamber provided with an air removal needle, the priming operation can be achieved by flowing blood into the drip chamber 4 as it is without inverting the drip chamber 4.

EXAMPLES

Hereinafter, the present invention will be illustrated in detail by examples. However, the present invention should not be construed as being limited thereto.

As described in Comparative Example 1 and Examples 1 to 5, filtration of a leucocyte containing liquid through a leucocyte removal filter was performed using the apparatus as shown in FIG. 1 and one of the blood administration sets shown in FIG. 2A to FIG. 5. NO concentration and oxygen partial pressures in the blood components before and after passing the leucocyte removal filter were continuously measured. Further, the blood components after passing the leucocyte removal filter were administered intravenously to an animal and the influence thereof on blood pressure was observed.

Comparative Example 1

In the apparatus as shown in FIG. 1, rabbit venous blood (NO concentration: 2 $\mu$mol/L, oxygen partial pressure: 83 mmHg ($1.11 \times 10^4$ Pa), the same being applied to Examples 1 to 4) in the blood bag 100 was introduced into a leucocyte removal filter 1 (comprising a leucocyte removal membrane material mainly composed of a polyurethane porous body, the same being applied to Examples 1 to 4) under the condition of QB 20 mL/minute, and an effluent is discharged from the leucocyte removal filter 1. Then, NO concentration and oxygen partial pressure of the effluent, and blood pressure of an animal after administration of the effluent were measured as follows.

<Measurement of NO Concentration and Oxygen Partial Pressure>

NO electrodes 10 and 12 were provided in the passages upstream and downstream the leucocyte removal filter 1 such that the electrodes contact the liquid as shown in FIG. 1. Each of the electrodes was connected to an NO measurement apparatus (NO-501, manufactured by Intermedical Co.) incorporated in a measurement meter (not shown) by wiring (not shown). Then, NO concentrations in the liquid before and after passing the leucocyte removal filter 1 were continuously measured and the results obtained were recorded in an outer recorder (not shown).

Also, electrodes 11 and 13 were provided in the passages upstream and downstream the leucocyte removal filter 1 such that the electrodes contact the liquid as shown in FIG. 1. Each of the electrodes was connected to an oxygen partial pressure measurement apparatus ($PO_2$-100DW, manufactured by Intermedical Co.) incorporated in a measurement meter (not shown) by wiring (not shown). Then, oxygen partial pressures in the liquid before and after passing the leucocyte removal filter 1 were continuously measured and the results obtained were recorded in an outer recorder (not shown).

<Measurement of Blood Pressure in Animal after Administration>

To a femoral artery of a rabbit (female, weighing 2.1 kg, different individual from the rabbit used for preparing an effluent) fixed on the back to Kitajima-type fixed way without anesthesia was inserted an indwelling catheter having an inner diameter of 1.65 mm and ligated. Thereafter, the catheter was connected to a pressure transducer (TP-00T, manufactured by Nihon Kohden Corporation), and the above-mentioned effluent was injected intravenously through an indwelling needle indwelled in an auricular vein of the rabbit. The blood pressure was measured and the results obtained were recorded by a pressure monitor.

In the examples rabbit was used as the test animal. Alternatively, other animals such as rat, dog, cat, pig, goat, sheep, monkey, ferret and other mammals may be used.

In Comparative Example 1, the first fraction contained no contamination of erythrocytes and colorless and transparent upon visual observation. The first fraction from the initiation of filtration until 5 mL flew out had an NO concentration of 20 mol/L (maximum value). In the animal administration test, blood depression of the maximum value of 30 mmHg occurred due to the effect of the first fraction.

At the stage where contamination of erythrocytes in the filtrate started, a decrease in NO concentration and an increase in oxygen partial pressure occurred. In an erythrocyte rich state, the NO concentration was recovered to about 2 $\mu$mol/L and oxygen pressure was 80 Pa. In the animal administration test, the blood pressure was recovered.

Example 1

Use was made of the blood administration set 200 of the present invention incorporated therein the device 210 for removing the first fraction as schematically illustrated in FIGS. 2A, 2B and 2C. The capacity of the leucocyte removal filter 1 was 50 mL and the capacity of the liquid pool space 18 was 5 mL.

In the state where the drip chamber 14 was inverted upside down as shown in FIG. 2A, clamp 6 was opened according to the conventional method and rabbit venous blood was introduced into the leucocyte removal filter 1. As shown in FIG. 2B, the effluent from the leucocyte removal filter 1 was pooled in an amount of 5 mL so that it did not go beyond the position of the scale 17 (indicating the maximum pool amount of liquid, 5 mL, of the liquid pool space 18) and the clamp 6 was closed. Then, as shown in FIG. 2C, the drip chamber 14 was returned to the normal state with respect to the upside and downside relationship and the effluent was pooled in the liquid pool space 18. Thereafter, the clamp 6 was opened and the effluent was discharged from the leucocyte removal filter 1 through the drip port 5 and the tube 15. Then, NO concentration and oxygen partial pressure of the effluent, and blood pressure of animal after administration were measured in the same manner as in Comparative Example 1.

The effluent had an NO concentration of 2.4 $\mu$mol/L and an oxygen partial pressure of 82 Pa. Therefore, they showed no change as compared with the blood before the filtration. That is, the effluent obtained was the leucocyte-free blood preparation of the present invention.

Also, in the animal administration test, no change in blood pressure was observed.

Example 2

Use was made of the blood administration set 300 of the present invention incorporated therein the device 310 for removing the first fraction as schematically illustrated in FIGS. 3A, 3B and 3C. The capacity of the leucocyte removal filter 1 was 50 mL and the capacity of the liquid pool space 23 was 5 mL. In the liquid pool space 23 was provided a cylindrical porous sintered body of polyethylene containing 0.1 g of crosslinked polyacrylic acid polymer. Though not shown, a lattice-type stopper was provided on an inner wall of the drip chamber 19 so that the fall of the absorbent could be prevented when the drip chamber 19 was returned to a normal state with respect to the upside and downside relationship as shown in FIG. 3C.

In the state where the drip chamber 19 was inverted upside down as shown in FIG. 3A, clamp 6 was opened according to the conventional method and rabbit venous blood was introduced into the leucocyte removal filter 1. As shown in FIG. 3B, the effluent from the leucocyte removal filter 1 was pooled in the liquid pool space 23 and the effluent was absorbed by the absorbent provided in the liquid pool space 23. The effluent from the leucocyte removal filter 1 was pooled in an amount of 5 mL so that it did not go beyond the position of the scale 22 (indicating the maximum pool amount of liquid, 5 mL, of the liquid pool space 23). After completion of the absorption, the clamp 6 was closed. Then, as shown in FIG. 3C, the drip chamber 19 was returned to the normal state with respect to the upside and downside. Thereafter, the clamp 6 was opened and the effluent was discharged from the leucocyte removal filter 1. Then, NO concentration and oxygen partial pressure of the effluent, and blood pressure of animal after administration were measured in the same manner as in Comparative Example 1.

The effluent had an NO concentration of 2.2 $\mu$mol/L and an oxygen partial pressure of 84 Pa. Therefore, they showed no change as compared with the blood before the filtration. That is, the effluent obtained was the leucocyte-free blood preparation of the present invention.

Also, in the animal administration test, no change in blood pressure was observed.

Example 3

Use was made of the blood administration set 400 of the present invention incorporated therein the device 410 for removing the first fraction as schematically illustrated in FIG. 4. The capacity of the leucocyte removal filter 1 was 50 mL and the inner volume of the bag 25 was 15 mL.

In the state where the single action clamp 26 was closed and the single action clamp 28 was open, rabbit venous blood was introduced into the leucocyte removal filter 1. About 10 mL of the effluent from the leucocyte removal filter 1 was pooled in the bag 25. After completion of discharge of the first fraction, the single action clamp 28 was closed and the single action clamp 26 was opened and further the clamp 6 was opened to discharge the effluent from the leucocyte removal filter 1. Then, NO concentration and oxygen partial pressure of the effluent, and blood pressure of animal after administration were measured in the same manner as in Comparative Example 1.

The effluent had an NO concentration of 2.4 $\mu$mol/L and an oxygen partial pressure of 83 Pa. Therefore, they showed no change as compared with the blood before the filtration. That is, the effluent obtained was the leucocyte-free blood preparation of the present invention.

Also, in the animal administration test, no change in blood pressure was observed.

Example 4

Use was made of the blood administration set 500 of the present invention incorporated therein the device 510 for removing the first fraction as schematically illustrated in FIG. 5. The capacity of the leucocyte removal filter 1 was 50 mL and the inner volume of the bag 25 was 15 mL.

In the state where the two-way cock 29 was communicated with the connection tube 27, rabbit venous blood was introduced into the leucocyte removal filter 1. About 10 mL of the effluent from the leucocyte removal filter 1 was pooled in the bag 25. After completion of discharge of the first fraction, the two-way cock 29 was communicated with the connection tube 8 and further the clamp 6 was opened to discharge the effluent from the leucocyte removal filter 1. Then, NO concentration and oxygen partial pressure of the effluent, and blood pressure of animal after administration were measured in the same manner as in Comparative Example 1.

The effluent had an NO concentration of 2.1 $\mu$mol/L and an oxygen partial pressure of 80 Pa. Therefore, they showed no change as compared with the blood before the filtration. That is, the effluent obtained was the leucocyte-free blood preparation of the present invention.

Also, in the animal administration test, no change in blood pressure was observed.

Example 5

Use was made of the blood administration set 200 of the present invention incorporated therein the device 210 for removing the first fraction as schematically illustrated in FIGS. 2A, 2B and 2C. The capacity of the leucocyte removal filter 1 was 50 mL and the capacity of the liquid pool space 18 was 5 mL. In the liquid pool space 18, nonwoven fabric that was coated with 0.3 g of crosslinked polyaspartic acid polymer and rounded into a cylinder was inserted in the drip chamber 14 along its inner wall.

In the state where the drip chamber 14 was inverted upside down as shown in FIG. 2A, clamp 6 was opened according to the conventional method and rabbit venous blood was introduced into the leucocyte removal filter 1. As shown in FIG. 2B, the effluent from the leucocyte removal filter 1 was pooled in an amount of 5 mL so that it did not go beyond the position of the scale 17 (indicating the maximum pool amount of liquid, 5 mL, of the liquid pool space 18) and the clamp 6 was closed. Then, as shown in FIG. 2C, the drip chamber 14 was returned to the normal state with respect to the upside and downside relationship. The effluent was pooled in the liquid pool space 18 and absorbed by the absorbent provided in the liquid pool space 18. Thereafter, the clamp 6 was opened and the effluent was discharged from the leucocyte removal filter 1 through the drip port 5 and tube 15. Then, NO concentration and oxygen partial pressure of the effluent, and blood pressure of animal after administration were measured in the same manner as in Comparative Example 1.

The effluent had an NO concentration of 2.1 $\mu$mol/L and an oxygen partial pressure of 85 Pa. Therefore, they showed no change as compared with the blood before the filtration. That is, the effluent obtained was the leucocyte-free blood preparation of the present invention.

Also, in the animal administration test, no change in blood pressure was observed.

What is claimed is:

1. A method for performing transfusion using a blood administration set having a leucocyte removal filter comprising the steps of:

introducing a leucocyte containing liquid into a leucocyte removal filter;

removing a first fraction from a leucocyte-free blood that is discharged from the leucocyte removal filter to avoid side effects that would otherwise occur when transfusion is performed;

performing transfusion of leucocyte-free blood that is discharged from the leucocyte removal filter after the first fraction.

2. A method according to claim 1, wherein the blood administration set comprises a passage for discharging the leucocyte-free blood from the leucocyte removal filter, and the passage comprises a device having a liquid pool space for removing the first fraction from the leucocyte-free blood discharged from the leucocyte removal filter.

3. A method according to claim 2, wherein an absorbent is provided in the liquid pool space for absorbing the first fraction.

4. A blood administration set for performing transfusion comprising:

a leucocyte removal filter having an inlet port for introducing a leucocyte containing liquid, for separating leucocytes from the leucocyte containing liquid; and a passage for a leucocyte-free blood that is discharged from the leucocyte removal filter;

wherein the passage comprises a device having a liquid pool space for removing a first fraction from leucocyte-free blood discharged from the leucocyte removal filter to avoid side effects that would otherwise occur when transfusion is performed.

5. A blood administration set according to claim 4, wherein the device for removing the first fraction comprises:

a cylindrical casing;

an inlet port provided upstream of the casing communicated with the leucocyte removal filter;

an outlet port provided downstream of the casing; and a tube provided inside the casing, having one end that is liquid-tightly bonded to the casing so as to open in the outlet port of the casing and the other end that extends to a predetermined position at an interval of a first space toward the inlet port of the casing, and the liquid pool space being defined by an inner wall of the casing and an outer wall of the tube for pooling the first fraction.

6. A blood administration set according to claim 4, wherein the device for removing the first fraction comprises:

a cylindrical casing;

an inlet port provided upstream of the casing communicated with the leucocyte removal filter;

an outlet port provided downstream of the casing;

a tube provided inside the casing, having one end that is liquid-tightly bonded to the casing so as to open in the inlet port of the casing and the other end that extends to a predetermined position at an interval of a first space toward the outlet port of the casing, the liquid pool space defined by an inner wall of the casing and an outer wall of the tube for pooling the first fraction; and an absorbent provided in the liquid pool space.

7. A blood administration set according to claim 4, wherein an absorbent is provided in the liquid pool space, for absorbing the first fraction.

* * * * *